United States Patent
Tsuji (10) Patent No.: US 10,234,628 B2
(45) Date of Patent: Mar. 19, 2019

(54) METHOD FOR PRODUCING SEMICONDUCTOR DEVICE

(71) Applicant: SUMITOMO ELECTRIC INDUSTRIES, LTD., Chuo-ku, Osaka-shi (JP)

(72) Inventor: Yukihiro Tsuji, Tama (JP)

(73) Assignee: SUMITOMO ELECTRIC INDUSTRIES, LTD., Osaka (JP)

( * ) Notice: Subject to any disclaimer, the term of this patent is extended or adjusted under 35 U.S.C. 154(b) by 6 days.

(21) Appl. No.: 15/714,790

(22) Filed: Sep. 25, 2017

(65) Prior Publication Data

US 2018/0149809 A1    May 31, 2018

(30) Foreign Application Priority Data

Nov. 28, 2016  (JP) ................................. 2016-230203

(51) Int. Cl.
| | |
|---|---|
| G02B 6/122 | (2006.01) |
| H01L 21/02 | (2006.01) |
| G01J 3/28 | (2006.01) |
| H01L 21/3213 | (2006.01) |
| G01N 21/956 | (2006.01) |

(Continued)

(52) U.S. Cl.
CPC .............. *G02B 6/122* (2013.01); *G01J 3/28* (2013.01); *G01N 21/956* (2013.01); *G03F 1/36* (2013.01); *G03F 7/70508* (2013.01); *H01L 21/02109* (2013.01); *H01L 21/3065* (2013.01); *H01L 21/32139* (2013.01)

(58) Field of Classification Search
None
See application file for complete search history.

(56) References Cited

U.S. PATENT DOCUMENTS

| | | | | |
|---|---|---|---|---|
| 4,948,259 A | * | 8/1990 | Enke ................... | G01B 11/0683 204/192.33 |
| 6,174,749 B1 | * | 1/2001 | Yuen ................... | H01S 5/18358 257/E33.069 |

(Continued)

FOREIGN PATENT DOCUMENTS

| | | | | |
|---|---|---|---|---|
| JP | 200193885 A1 | * | 4/2001 | ............... G01B 9/02 |
| JP | 2008-28370 | | 2/2008 | |

*Primary Examiner* — Shamim Ahmed (74) *Attorney, Agent, or Firm* — Smith, Gambrell & Russell, LLP.

(57) ABSTRACT

A method for producing a semiconductor device includes the steps of: providing a substrate product including a substrate and a first stacked semiconductor layer disposed on the substrate, the first stacked semiconductor layer including a plurality of semiconductor layers having different compositions that are alternately and periodically stacked with a predetermined period; forming a mask on the substrate product; and etching the first stacked semiconductor layer using the mask. The step of etching the first stacked semiconductor layer includes the steps of: optically monitoring an optical signal including a light component reflected from an etched surface of the substrate product for detecting an endpoint of etching; converting the optical signal to an electric signal to generate a monitoring signal; performing Fourier transform on the monitoring signal to generate a spectrum signal; and determining the endpoint detection of the etching by using the spectrum signal provided by the Fourier transform.

6 Claims, 9 Drawing Sheets

(51) Int. Cl.
*G03F 7/20* (2006.01)
*G03F 1/36* (2012.01)
*H01L 21/3065* (2006.01)

(56) References Cited

U.S. PATENT DOCUMENTS

| | | | | |
|---|---|---|---|---|
| 6,876,455 | B1* | 4/2005 | Katz | G01B 11/0625 |
| | | | | 356/503 |
| 2004/0081498 | A1* | 4/2004 | Tu | B41J 2/465 |
| | | | | 400/118.2 |
| 2004/0203177 | A1* | 10/2004 | Davis | G03F 7/70625 |
| | | | | 438/14 |
| 2013/0314692 | A1* | 11/2013 | Goto | G01B 11/0625 |
| | | | | 356/4.09 |
| 2015/0131691 | A1* | 5/2015 | Lee | H01S 5/18341 |
| | | | | 372/50.11 |
| 2016/0260869 | A1* | 9/2016 | Jeon | H01L 33/38 |
| 2017/0256463 | A1* | 9/2017 | Bailey, III | H01L 22/12 |

* cited by examiner

METHOD FOR PRODUCING SEMICONDUCTOR DEVICE

BACKGROUND OF THE INVENTION

1. Field of the Invention

The present invention relates to a method for producing a semiconductor device.

2. Description of the Related Art

Japanese Unexamined Patent Application Publication No. 2008-28370 discloses a surface-emitting laser.

SUMMARY OF THE INVENTION

Semiconductor devices include a stacked semiconductor layer that includes a plurality of semiconductor layers stacked alternately. For example, a vertical cavity surface-emitting laser (VCSEL) includes a stacked semiconductor layer for forming the distributed Bragg reflector. When the stacked semiconductor layer is etched, the endpoint of etching needs to be detected. When the endpoint of etching is precisely detected, the semiconductor devices having stable characteristics may be produced. For example, in a process of etching a stacked semiconductor layer for forming a lower distributed Bragg reflector of the vertical cavity surface-emitting laser, endpoint detection is required. The stacked semiconductor layer for forming the distributed Bragg reflector includes a plurality of semiconductor layers having different compositions that are alternately stacked.

The endpoint detection is performed by either a plasma monitoring method or an optical interference method. In the plasma monitoring method, the endpoint detection of etching is performed while the emission spectra of elements (ions) in plasma are monitored during the etching. Specifically, a change in the intensity of the emission spectra during the etching is detected. In the optical interference method, the endpoint detection of etching is performed while a change in reflected light from a product being etched is monitored for a predetermined duration of etching. Specifically, the number of changes in the intensity of interference light contained in reflected light is counted while etching is performed. These endpoint detection methods have the following restrictions. In the plasma monitoring method, a semiconductor layer at which etching is to be stopped needs to contain an element that can be detected by plasma monitoring. In the optical interference method, a semiconductor layer is required from which the top or bottom of an interference pattern is counted.

A method for producing a semiconductor device according to an aspect of the present invention includes the steps of providing a substrate product including a substrate and a first stacked semiconductor layer disposed on the substrate, the first stacked semiconductor layer including a plurality of semiconductor layers having different compositions that are alternately and periodically stacked with a predetermined period; forming a mask on the substrate product; and etching the first stacked semiconductor layer using the mask. In addition, the step of etching the first stacked semiconductor layer includes the steps of optically monitoring an optical signal including a light component reflected from an etched surface of the substrate product for detecting an endpoint of etching; converting the optical signal to an electric signal to generate a monitoring signal; performing Fourier transform on the monitoring signal to generate a spectrum signal; and determining the endpoint detection of the etching by using the spectrum signal provided by the Fourier transform.

Objects, features, and advantages according to embodiments of the present invention will be more easily understood from the following detailed descriptions of preferred embodiments according to the present invention with reference to the attached drawings.

DESCRIPTION OF THE PREFERRED EMBODIMENTS

Some embodiments will be described.

A method for producing a semiconductor device according to an embodiment includes the steps of (a) providing a substrate product including a substrate and a first stacked semiconductor layer disposed on the substrate, the first stacked semiconductor layer including a plurality of semiconductor layers having different compositions that are alternately and periodically stacked with a predetermined period; (b) forming a mask on the substrate product; and (c) etching the first stacked semiconductor layer using the mask. In addition, the step of etching the first stacked semiconductor layer includes the steps of optically monitoring an optical signal including a light component reflected from an etched surface of the substrate product for detecting an endpoint of etching; converting the optical signal to an electric signal to generate a monitoring signal; performing Fourier transform on the monitoring signal to generate a spectrum signal; and determining the endpoint detection of the etching by using the spectrum signal provided by the Fourier transform.

According to the method for producing a semiconductor device, an optical signal including a light component reflected from an etched surface of the substrate product is used for detecting an endpoint of etching. Specifically, the optical signal used for detecting an endpoint of etching contains interference light including depth information of a surface (a surface of the first stacked semiconductor layer) of the substrate product being etched. The intensity of the interference light varies in a process of etching the first stacked semiconductor layer. The optical signal is converted to an electric signal to generate a monitoring signal. Fourier transform is performed on the monitoring signal to generate a spectrum signal. The spectrum signal obtained by performing Fourier transform on the monitoring signal includes a frequency component in a frequency axis that corresponds to a change of the intensity of the interference light in a time axis. The magnitude of a frequency component at a certain time during etching relates to a layer structure in the first stacked semiconductor layer that is being etched at the certain time and has been etched until the certain time. Therefore, the endpoint detection of the etching is determined by using the spectrum signal provided by the Fourier transform.

In the method for producing a semiconductor device according to an embodiment, the optical signal may include an optical interference signal that is obtained through interference between the light component reflected from the etched surface and a light component reflected from a surface of the substrate.

In the method for producing a semiconductor device according to an embodiment, preferably, the substrate product includes a device area and an accessory area. The mask has a plurality of patterns including openings on the device area and the accessory area. The pattern on the accessory area has a larger opening than that of the pattern on the device area so that the accessory area is etched at a larger etching rate than that of the device area. In addition, the optical signal for detecting the endpoint of the etching contains the light component reflected from the etched surface in the accessory area.

According to the method for producing a semiconductor device, the mask has a plurality of patterns including openings on the device area and the accessory area. The etching rate in a process of etching the first stacked semiconductor layer relates to an opening area of the mask. The difference between the etching rate in the accessory area and the etching rate in the device area may be adjusted by changing the opening areas of the mask in the accessory area and the device area. By using this, the overetching time may be controlled on the basis of the endpoint detection with the optical signal containing the light component reflected from the etched surface in the accessory area.

In the method for producing a semiconductor device according to an embodiment, the substrate product may include an active layer that generates light. The first stacked semiconductor layer may be disposed between the substrate and the active layer.

According to the method for producing a semiconductor device, the semiconductor device may include a semiconductor light-emitting device including the active layer.

In the method for producing a semiconductor device according to an embodiment, preferably, the substrate product includes a second stacked semiconductor layer disposed on the substrate, the second stacked semiconductor layer including a plurality of semiconductor layers having different compositions that are alternately and periodically stacked. The active layer is disposed between the first stacked semiconductor layer and the second stacked semiconductor layer. In addition, each of the first stacked semiconductor layer and the second stacked semiconductor layer has a periodic structure that constitutes a distributed Bragg reflector.

According to the method for producing a semiconductor device, the semiconductor device may include a distributed Bragg reflector.

In the method for producing a semiconductor device according to an embodiment, preferably, the first stacked semiconductor layer includes a first portion including a plurality of semiconductor layers alternately stacked, a contact layer, and a second portion including a plurality of semiconductor layers alternately stacked. The first portion is disposed between the contact layer and the substrate. The contact layer is disposed between the first portion and the second portion. In addition, in the step of etching the first stacked semiconductor layer, the etching is stopped in the contact layer in response to determining the endpoint detection of the etching.

According to the method for producing a semiconductor device, etching may be stopped in the contact layer of the first stacked semiconductor layer in response to determining the endpoint detection of the etching.

In the method for producing a semiconductor device according to an embodiment, the spectrum signal may include a frequency component corresponding to the period of the semiconductor layers in the first stacked semiconductor layer. In addition, in the step of determining the endpoint detection of the etching, the etching may be stopped by detecting a change in the spectrum signal.

The findings of the present invention can be easily understood by considering the following detailed description with reference to the attached drawings which are illustrated as examples. Embodiments of a method for producing a semiconductor device and a semiconductor device will now be described with reference to the attached drawings. If possible, the same parts are designated by the same reference numerals.

Figure 1:
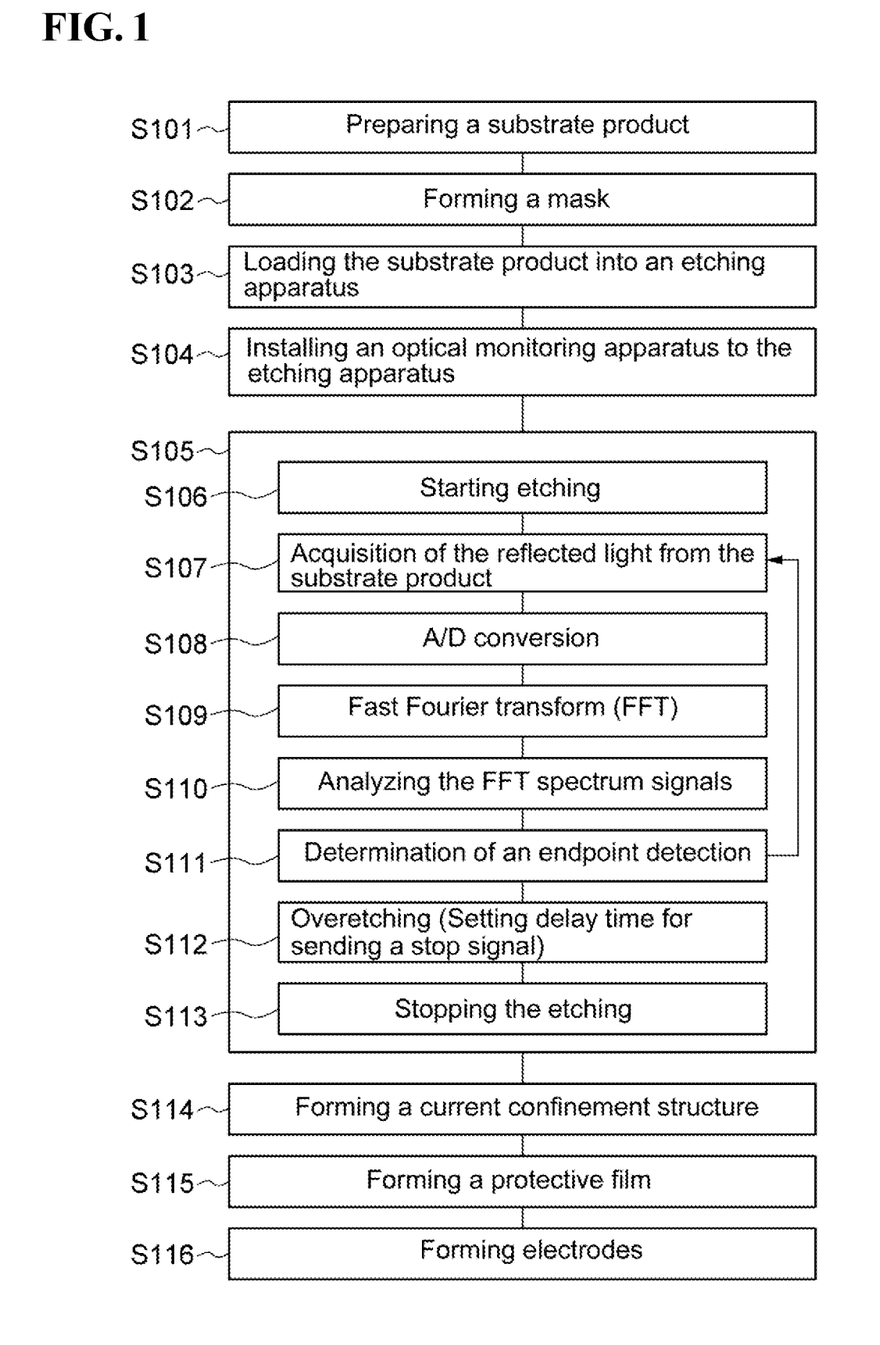
FIG. 1 illustrates a process flow including principal steps in a method for producing a semiconductor device according to this embodiment.

FIG. 1 illustrates a process flow including principal steps in a method for producing a semiconductor device according to this embodiment. FIGS. 2A and 2B and FIGS. 3A, 3B, and 3C schematically illustrate principal steps in the method for producing a semiconductor device according to this embodiment.

The method for producing a semiconductor device according to this embodiment will be described with reference to FIG. 1, FIGS. 2A and 2B, and FIGS. 3A to 3C.

Figure 2A:
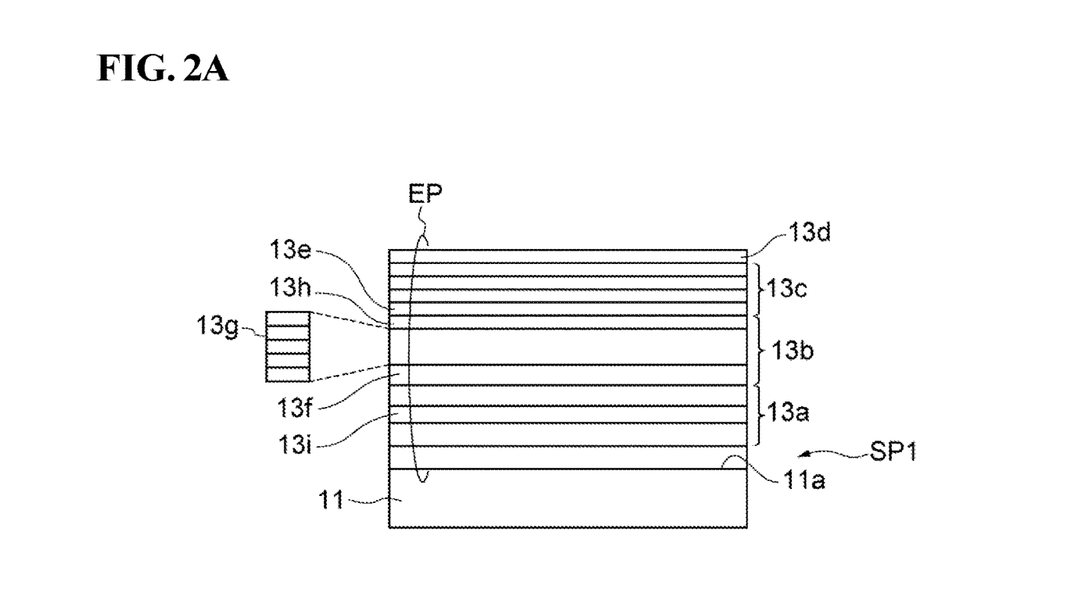
FIGS. 2A and 2B schematically illustrate principal steps in the method for producing a semiconductor device according to this embodiment.

In Step S101, as illustrated in FIG. 2A, a first substrate product SP1 is provided. An epitaxial region EP is grown on a substrate 11 to form the first substrate product SP1. The substrate 11 is, for example, a semiconductor wafer. In this embodiment, a first stacked semiconductor layer 13*a* for forming an optical reflector (for example, lower distributed Bragg reflector), a semiconductor region 13*b* for forming an active layer, a second stacked semiconductor layer 13*c* for forming another optical reflector (for example, upper distributed Bragg reflector), and a semiconductor layer 13*d* for forming an upper contact layer are sequentially grown on a main surface 11*a* of the substrate 11. This growth is performed by using, for example, a metal-organic vapor phase epitaxy (MOVPE) method or a molecular beam epitaxy (MBE) method.

The first substrate product SP1 includes a semiconductor multilayer film which is represented by $Al(x)Ga(1-x)As$, where $0 \leq x \leq 1$ and x represents the Al content, and in which x changes periodically. The first substrate product SP1 includes the following:

a substrate 11: 4 inch n-type GaAs wafer;

a first stacked semiconductor layer 13*a* for forming a lower distributed Bragg reflector: Si-doped n-type superlattice, specifically, AlGaAs (Al content=0.12)/AlGaAs (Al content=0.90) with 35 pairs;

a semiconductor layer 13*i* for forming a contact layer: n-type GaAs layer (thickness: 150 nm to 500 nm);

a semiconductor region 13b for forming an active layer;

a lower spacer layer 13f: Si-doped n-type AlGaAs (Al content=0.30);

a quantum well structure 13g included in the active layer: GaAs/AlGaAs with 3 QWs;

an upper spacer layer 13h: undoped AlGaAs (Al content=0.30) and Zn-doped p-type AlGaAs (Al content=0.90);

an Al-containing semiconductor layer 13e for forming a current confinement layer: AlGaAs (Al content=0.98);

a second stacked semiconductor layer 13c for forming an optical reflector (an upper distributed Bragg reflector): Zn-doped p-type superlattice, specifically, AlGaAs (Al content=0.12)/AlGaAs (Al content=0.90) with 23 pairs; and a semiconductor layer 13d for forming an upper contact layer: Zn-doped p-type GaAs.

The epitaxial region EP includes a semiconductor film for forming a contact layer, an upper semiconductor region disposed above the semiconductor film for forming the contact layer, and a lower semiconductor region disposed below the semiconductor film for forming the contact layer. The semiconductor film for forming the contact layer has a thickness of 150 to 500 nm. The upper semiconductor region has a thickness of, for example, 4.5 to 5 µm. The lower semiconductor region has a thickness of, for example, 2 to 3 µm.

After the first substrate product SP1 is provided, the first substrate product SP1 is etched to form a semiconductor post. By detecting the endpoint, this etching is finished. When necessary, a mask may be used in the processing. The endpoint detection is also effective for etching that uses a mask.

Figure 2B:
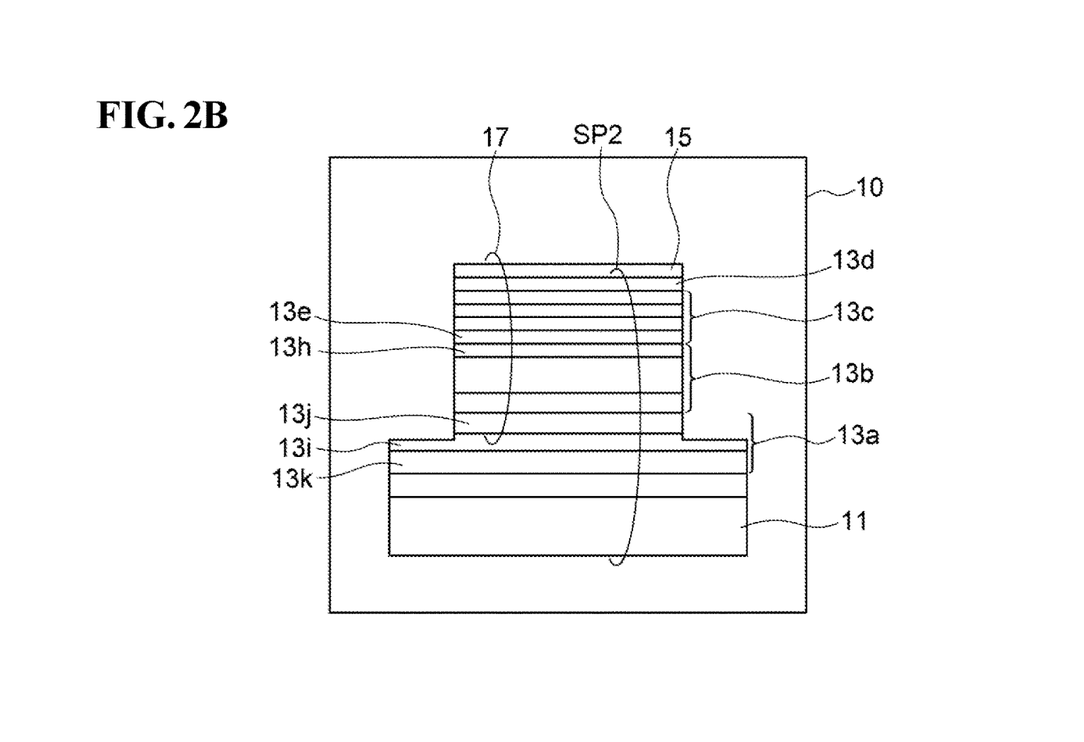
Figure 4A:
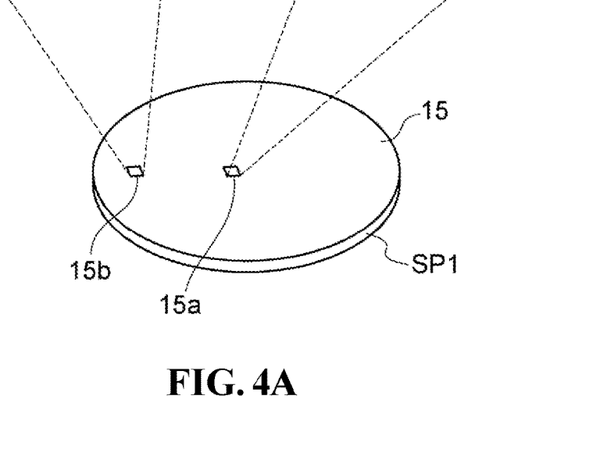
FIGS. 4A, 4B, and 4C illustrate a mask on a first substrate product.
Figure 4B:
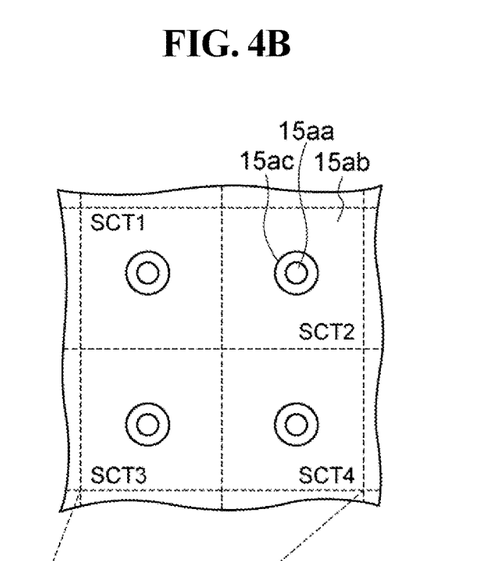

In this embodiment, a semiconductor mesa for forming the semiconductor post is formed by removing the second stacked semiconductor layer 13c, the semiconductor region 13b, and a part or the entirety of the first stacked semiconductor layer 13a. Specifically, in Step S102, a mask 15 is formed on a main surface of the first substrate product SP1 as illustrated in FIG. 2B. Then, the first substrate product SP1 with the mask 15 is placed in a processing apparatus 10. The mask 15 is made of, for example, a silicon-based inorganic insulator such as SiN. The mask 15 on the first substrate product SP1 includes a device array portion 15a and an accessory portion 15b as illustrated in FIG. 4A. The device array portion 15a has a pattern that defines the array of semiconductor devices to be produced. The accessory portion 15b has a pattern that defines a structure required during the etching process and after the etching process. FIG. 4B illustrates an enlarged device array portion 15a, and the enlarged portion includes four typical device sections SCT1, SCT2, SCT3, and SCT4. Each of the four device sections SCT1, SCT2, SCT3, and SCT4 includes a first pattern 15aa for forming a semiconductor post including principal parts of a vertical cavity surface-emitting laser, a second pattern 15ab for forming a terrace, and an opening 15ac that separates the first pattern 15aa from the second pattern 15ab.

The device array portion 15a includes a two-dimensional array of device sections. An example of the pattern is shown below.

The first pattern 15aa is disposed in the opening of the second pattern 15ab. The first pattern 15aa and the second pattern 15ab are disposed such that an annular opening is formed between the edge of the second pattern 15ab and the edge of the first pattern 15aa. The edge of the first pattern 15aa has a circular shape with a diameter of 25 µm. The width of the opening 15ac is 15 µm in a radial direction. The second pattern 15ab has a circular opening with a diameter of 55 µm.

Figure 4C:
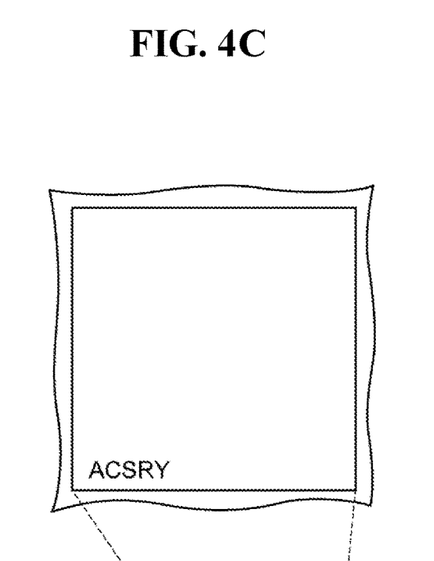

FIG. 4C illustrates an enlarged accessory portion 15b. In this embodiment, the accessory portion 15b has a pattern for optical monitoring used for the endpoint detection of etching. The pattern of the accessory portion 15b has an opening ACSRY that provides a large etching area to prevent a micro-loading effect. The opening ACSRY has a size of, for example, 500 µm×500 µm. The opening ACSRY suitably has sides with 500 µm or more or a diameter of 500 µm or more to obtain interference light applicable to monitoring. FIG. 4A illustrates an exemplary position of the accessory portion 15b on the first substrate product SP1. The mask 15 may include an accessory portion 15b disposed at a desired position.

Figure 5:
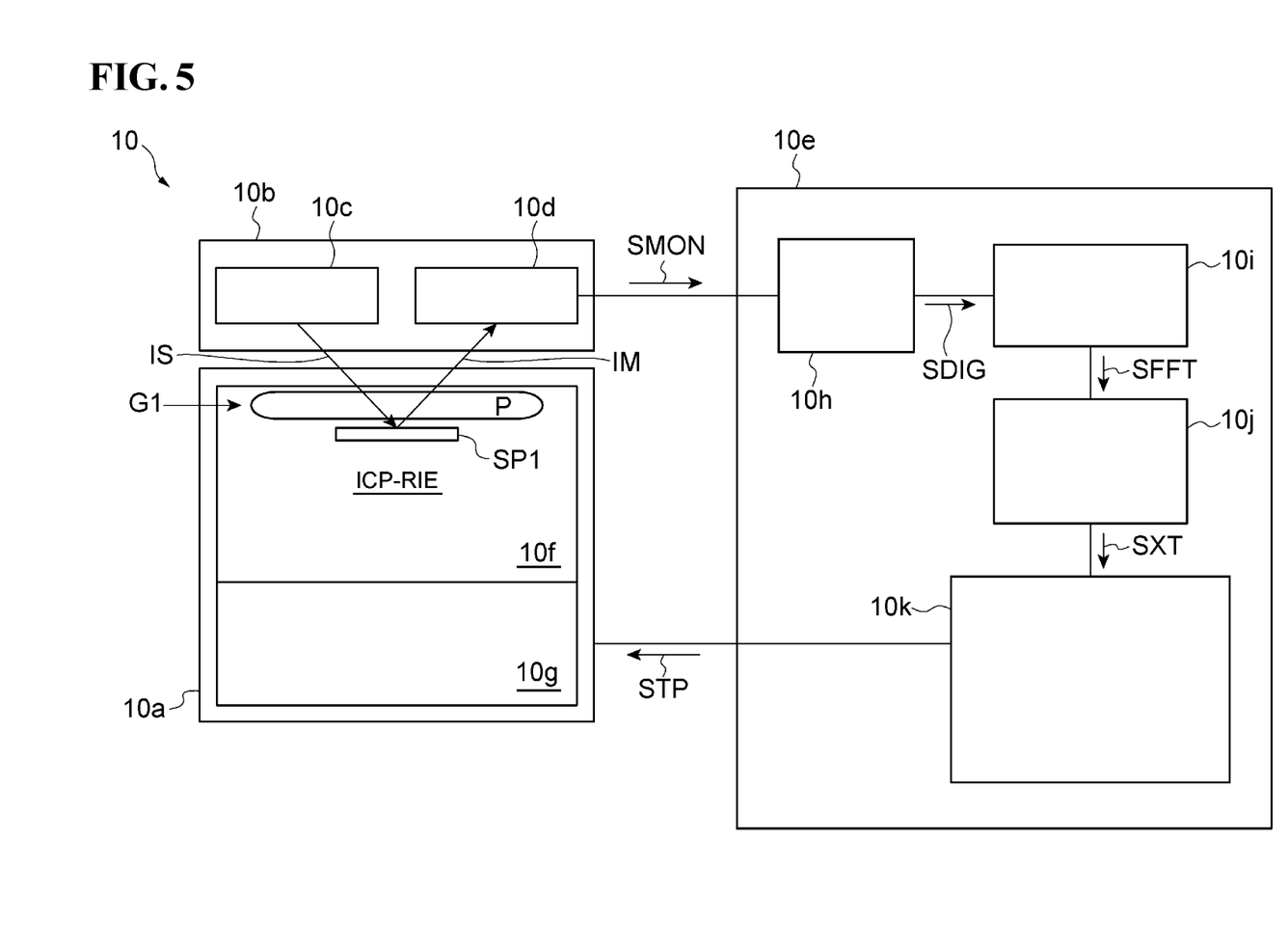
FIG. 5 schematically illustrates a configuration of an etching apparatus.

After the mask 15 is formed on the first substrate product SP1, in Step S103, the first substrate product SP1 is loaded into an etching apparatus 10a of the processing apparatus 10 as illustrated in FIG. 5. The etching apparatus 10a is, for example, an inductive coupled plasma reactive ion etching (ICP-RIE) apparatus.

In Step S104, an optical monitoring apparatus 10b is disposed with respect to the etching apparatus 10a as illustrated in FIG. 5. The optical monitoring apparatus 10b includes a light source 10c and a spectroscope 10d. The light source 10c and the spectroscope 10d of the optical monitoring apparatus 10b are subjected to alignment with the first substrate product SP1 in the etching apparatus 10a. As a result of the alignment, source light IS from the light source 10c is applied to a desired area (e.g., an opening ACSRY in the accessory portion) on the main surface of the first substrate product SP1 in the etching apparatus 10a. Furthermore, the spectroscope 10d receives reflected light IM from the desired area. When necessary, the reflected light IM from the device array portion 15a may be used for endpoint detection.

In this embodiment, the endpoint detection is performed by an optical interference method using the optical monitoring apparatus 10b. The optical monitoring apparatus 10b sends electric signals SMON for monitoring to a processing apparatus 10e.

Figure 6A:
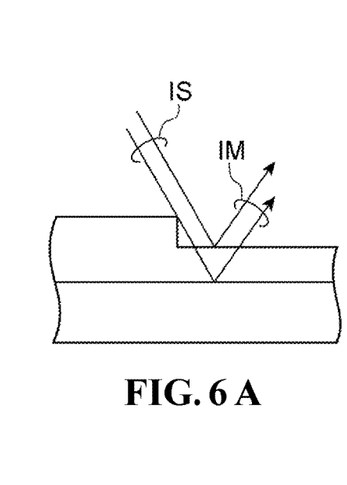
FIGS. 6A, 6B, 6C, and 6D illustrate a waveform of reflected light associated with endpoint detection and frequency spectra.
Figure 6B:
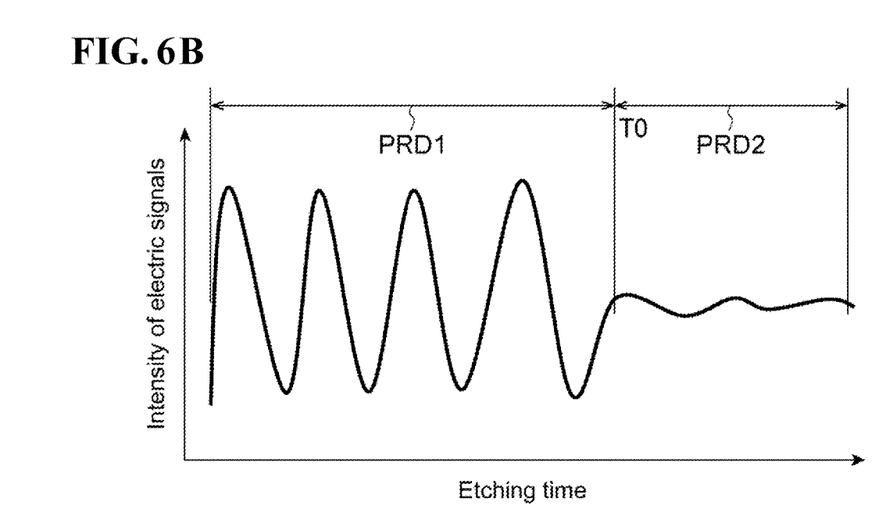

In Step S105, the epitaxial region EP is etched using the mask 15 to form a mesa-shaped semiconductor post 17. Specifically, in Step S106, an etchant G1 is supplied to a chamber 10f while the pressure in the chamber 10f is reduced. Plasma P of the etchant G1 is generated using power from a radio frequency power supply 15g to etch the epitaxial region EP. The acquisition of the reflected light IM (monitoring light for endpoint detection) with the optical monitoring apparatus 10b is started simultaneously with the start of etching or immediately after the start of etching. In Step S107, the spectroscope 10d of the optical monitoring apparatus 10b acquires the reflected light IM from a first substrate product SP1 being etched. As illustrated in FIG. 6A, the reflected light IM contains interference components of reflected light. One of the reflected light is reflected from a surface formed by etching or a surface being etched, and the other of the reflected light is reflected from a boundary in a semiconductor structure of a base (e.g., a boundary surface between an epitaxial layer and a substrate). The reflected light IM contains rays of light having various wavelengths corresponding to wavelength components of the source light IS. The spectroscope 10d selects a wavelength component with which the endpoint is easily detected and sends light having the selected wavelength component to a photodiode. The photodiode receives the light having the wavelength component and generates monitoring signals (referred to as electric signals SMON). The electric signals SMON are analog signals with information that indicates the intensity of the reflected light IM. The electric signals SMON are sent to an A/D conversion circuit 10h illustrated in FIG. 5. FIG. 6B illustrates a waveform of the electric signals SMON. The reflected light IM that enters the spectroscope 10d has substantially the same waveform as that of the electric signals SMON. In FIG. 6B, the vertical axis shows the intensity of the electric signals SMON and the horizontal axis shows the etching time. The waveform of the electric signals SMON in FIG. 6B shows the thickness information of a layer structure after the completion of etching of a stacked semiconductor layer for forming an upper distributed Bragg reflector and a stacked semiconductor layer for forming an active layer and also shows the thickness information of a layer structure during etching of a stacked semiconductor layer for forming a lower distributed Bragg reflector.

In Step S108, as illustrated in FIG. 5, the A/D conversion circuit 10h converts the electric signals SMON into digital signals SDIG that indicate the amplitude of the electric signals SMON. The waveform of the digital signals SDIG is substantially the same as the waveform of the electric signals SMON illustrated in FIG. 6B, except that the amplitude on the vertical axis has discrete values (e.g., 64-bit digital values). The waveform of the electric signals SMON periodically changes during the period PRD1 whereas the waveform substantially does not change during the period PRD2. During the period PRD1, a superlattice in the upper distributed Bragg reflector is etched. During the period PRD2, a GaAs contact layer having a larger thickness than a semiconductor layer (for example, GaAs layer or AlGaAs layer) in the superlattice in the upper distributed Bragg reflector is etched.

The digital signals SDIG are sent to a fast Fourier transform unit 10i. In Step S109, the fast Fourier transform unit (FFT unit) 10i illustrated in FIG. 5 generates spectrum signals SFFT that indicate a frequency spectrum in the Fourier space of the digital signals SDIG. The spectrum signals SFFT are generated by a so-called fast Fourier transform method. In this embodiment, the fast Fourier transform is performed by using commercially available hardware (e.g., an FFT analyzer such as CF-9200 manufactured by Ono Sokki Co., Ltd.). If possible, a part or all of FFT processing may be performed by replacing a part or all of hardware processing with processing of software produced using numerical computation language, such as MATLAB available from MATHWORKS.

Figure 6C:
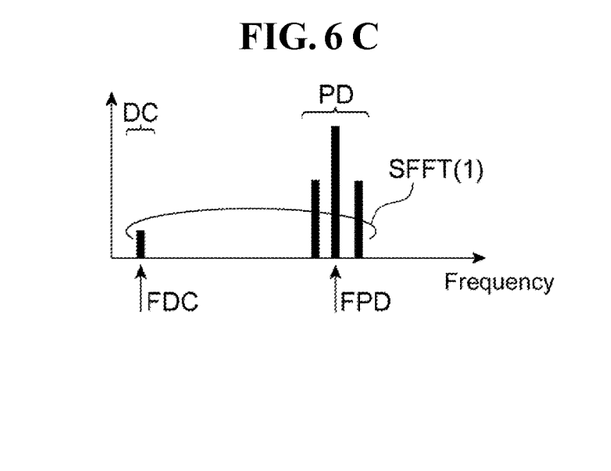
Figure 6D:
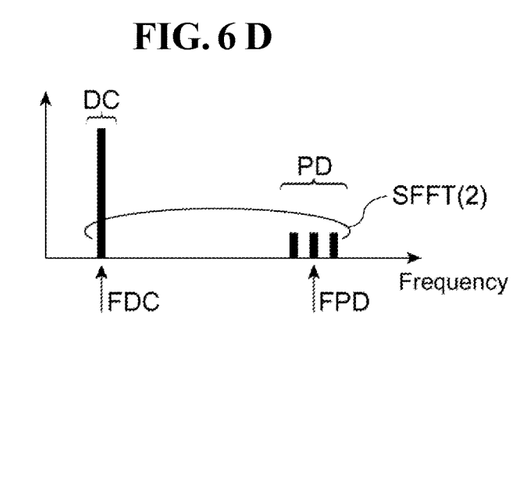

The endpoint detection of etching is determined on the basis of the computational results of fast Fourier transform. FIG. 6C illustrates a typical spectrum signal SFFT(1) of a digital signal SDIG in the period PRD1. FIG. 6D illustrates a typical spectrum signal SFFT(2) of a digital signal SDIG in the period PRD2. Specifically, FIG. 6D illustrates the spectrum signal SFFT(2) at a time after a short lapse of time from the boundary time T0 between the period PRD1 and the period PRD2. The spectrum signals SFFT(1) and SFFT(2) contain a frequency component PD at a frequency FPD corresponding to the period of the superlattice and a component DC at a frequency FDC that is sufficiently lower than the frequency FPD of the frequency component PD. In the spectrum signal SFFT(1), the intensity of the frequency component PD is larger than that of the component DC. On the other hand, in the spectrum signal SFFT(2), the intensity of the frequency component PD is smaller than that of the component DC. Such a change in the waveform enables the determination of the endpoint detection of etching with the spectrum signals SFFT.

Specifically, the spectrum signals SFFT are sent to an extraction unit 10j illustrated in FIG. 5. In Step S110, the extraction unit 10j acquires, on the frequency axis of fast Fourier transform, a spectrum signal value VPD at the frequency FPD and a spectrum signal value VDC at the frequency FDC. The extraction unit 10j is realized using, for example, system development software such as LabVIEW available from National Instruments.

These signal values are sent to a determination unit 10k illustrated in FIG. 5. In Step S111, the determination unit 10k determines the magnitude relation between the spectrum signal value VPD and the spectrum signal value VDC.

When a predetermined relation (e.g., the spectrum signal value VPD is lower than the spectrum signal value VDC) is not achieved in the determination with the determination unit 10k, the determination unit 10k determines that etching is still in progress. Herein, the determination unit 10k sends a control signal so that the processing apparatus 10e acquires electric signals SMON from the spectroscope 10d again in Step S107. Consequently, steps from Step S107 to Step S111 in FIG. 1 are repeatedly performed.

When the predetermined relation (e.g., the spectrum signal value VPD is lower than the spectrum signal value VDC) is achieved in the determination with the determination unit 10k, the determination unit 10k determines that the endpoint of etching is detected. The determination unit 10k sends a stop signal STP to the etching apparatus 10a in response to the determination.

When necessary, in Step S112, the determination unit 10k may, in response to the determination of endpoint detection, delay sending the stop signal STP until a predetermined delay time passes from a time of the determination of endpoint detection to control an amount of over-etching of the GaAs contact layer. After a lapse of a certain specified time (e.g., a setting delay time), the determination unit 10k may send the stop signal STP to the etching apparatus 10a.

In Step S113, the etching apparatus 10a stops the etching in response to the stop signal STP. Subsequently, the mask 15 is removed to form a second substrate product SP2.

In this production method, the reflected light IM from the first substrate product SP1 contains interference light concerning depth information of the surface of the first substrate product SP1 being etched (the surface of the first stacked semiconductor layer being etched). The intensity of the interference light in the reflected light IM varies in accordance with the structure in the first stacked semiconductor layer. The computational results obtained by performing Fourier transform on electric signals that indicate the intensity of the reflected light IM contain frequency components that indicate a change in the reflected light IM. Specifically, the magnitude of a frequency component at a certain time during etching relates to a layer structure of the first stacked semiconductor layer that has been etched until the certain time. During the etching of a periodical stacked semiconductor layer, the waveform of the intensity of reflected light contains a frequency component corresponding to the period. However, after the etching of the periodical stacked semiconductor layer, the computational results of Fourier transform contain a main component in a frequency region lower than the frequency of the frequency component corresponding to the period. The computational results of Fourier transform changes at a time when the etching of a periodical stacked semiconductor layer is completed. Therefore, the computational results obtained by performing Fourier transform on electric signals that indicate the intensity of the reflected light IM may provide information for the endpoint detection of etching.

As illustrated in FIG. 2B, the first stacked semiconductor layer 13a includes a first portion 13j including a plurality of semiconductor layers alternately stacked on top of one another, a contact layer 13i, and a second portion 13k including a plurality of semiconductor layers alternately stacked on top of one another. The contact layer 13i is disposed between the first portion 13j and the second portion 13k. The second portion 13k is disposed between the contact layer 13i and the substrate 11. The contact layer 13i is disposed between the substrate 11 and the first portion 13j.

During the etching of the first portion 13j having a periodic structure, the reflected light IM contains a frequency component corresponding to the periodic structure. After the completion of the etching of the first portion 13j, the intensity of the reflected light IM decreases, and this change in intensity leads to a change in frequency components. This change in frequency components is detected from the computational results of the Fourier transform. According to the endpoint detection that uses Fourier transform computational results, etching is stopped with desired accuracy in the contact layer 13i without counting the number of peaks that appear in an interference light waveform. This reduces a variation in the thickness of the remaining etched contact layer 13i. Furthermore, a layer having a thickness required for contact may be left with certainty. Therefore, the thickness of the semiconductor film required for forming a contact layer can be decreased as much as possible, and the contact layer can have a necessary thickness with certainty.

In this method for producing a semiconductor device, the endpoint of etching is determined on the basis of the information obtained by optically reading the shape of a structure formed by the etching. Specifically, in response to the end of etching of the periodic structure, the Fourier transform computational results show a decrease in the amplitude of a frequency component resulting from the periodic structure of the first portion 13j. Simultaneously, the Fourier transform computational results show an increase in the amplitude of a component resulting from a semiconductor region (a semiconductor region having no periodic structure). By determining the changes in the frequency components, etching may be stopped in the contact layer 13i in the first stacked semiconductor layer 13a. Consequently, the etched contact layer 13i may be provided with a desired thickness and a desired etching amount. A thin contact layer 13i having a thickness of, for example, 150 nm or less, may be formed in the first stacked semiconductor layer 13a with high reproducibility. Thus, a thin contact layer 13i in a lower distributed Bragg reflector (DBR) of vertical cavity surface-emitting lasers may be provided. Such a thin contact layer 13i also exhibits small light absorption. The contact layer 13i is formed of a semiconductor material such as GaAs or Al(x)Ga(1−x) having an Al content of $0 \leq x \leq 0.3$.

Figure 7A:
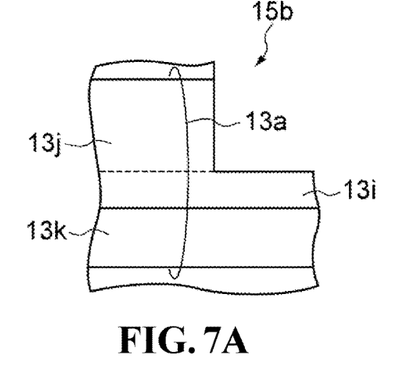
FIGS. 7A, 7B, and 7C illustrate the progress of etching in a device array portion and an accessory portion of the mask described with reference to FIGS. 4A, 4B, and 4C.
Figure 7B:
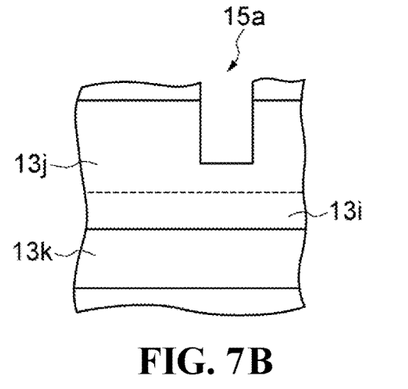

FIGS. 7A and 7B illustrate the progress of etching in the device array portion 15a and accessory portion 15b of the mask 15 described with reference to FIGS. 4A, 4B, and 4C. The first substrate product SP1 includes a device area corresponding to the device array portion 15a and an accessory area corresponding to the accessory portion 15b. The device area and the accessory area are defined by the mask 15.

Referring to FIG. 7A, etching in the accessory portion 15b reaches its endpoint. Herein, the reflected light IM from the accessory portion 15b contains a signal indicating the endpoint of etching. Referring to FIG. 7B, etching in the device array portion 15a does not reach its endpoint. In the etching, the etching rate in the accessory portion 15b is higher than that in the device array portion 15a due to a micro-loading effect. In the embodiment, the etching rate in the accessory portion 15b is set to be 300 nm to 400 nm per minute, for example.

Figure 7C:
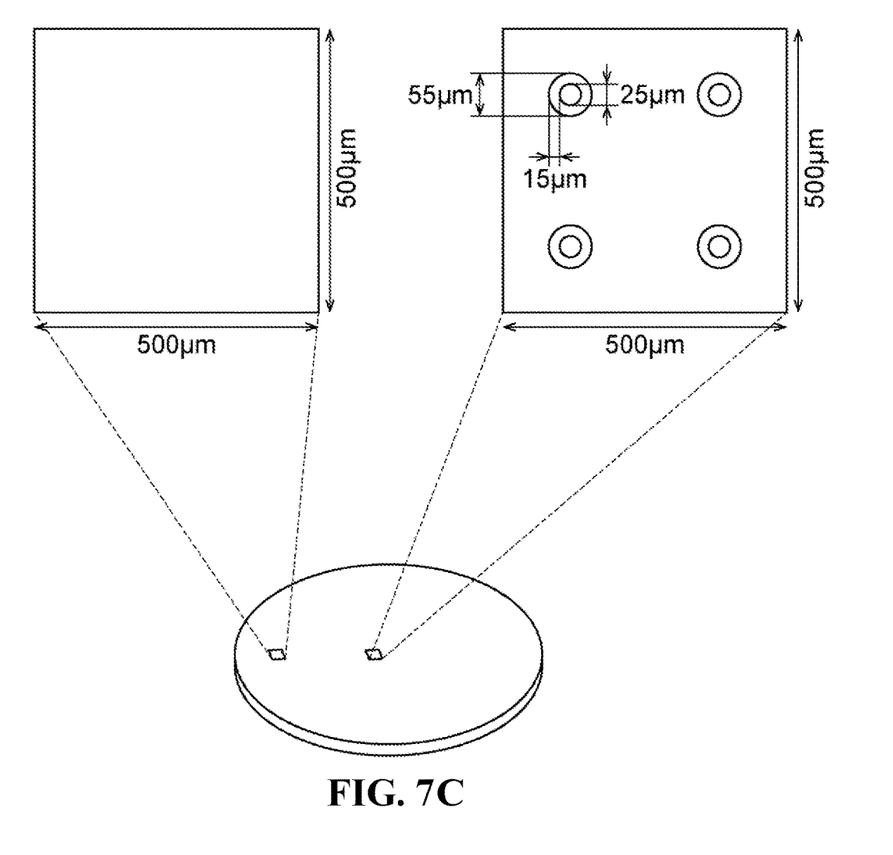

Referring to FIGS. 7A and 7C, the accessory portion 15b has an opening with an area (e.g., 500 μm×500 μm) including, for example, four device sections. In the mask 15, the area ratio (opening ratio) of an opening per device section is, for example, about 0.03. The etching rate in the device array portion 15a is about 0.8 times the etching rate in the accessory portion 15b. The opening ratio in the accessory portion 15b of the mask 15 is larger than that of the device array portion 15a. The etching rates in the device array portion 15a and the accessory portion 15b are dependent on the opening ratio of each region. The opening ratio in the device array portion 15a is defined in accordance with the design of individual devices. On the other hand, the opening ratio in the accessory portion 15b may be independently changed regardless of the device design. That is, the etching rate in the accessory portion 15b may be controlled to a desired etching rate by adjusting the opening ratio.

As described above, the monitoring light for endpoint detection is not acquired from the device array portion 15a in which the opening ratio is dependent on the design of individual devices, but is acquired from the accessory portion 15b. According to the method for producing a semiconductor device, the difference in etching rate between the accessory portion 15b and the device array portion 15a may be adjusted by the pattern of the mask 15. For example, by using the difference in etching rate between the accessory portion 15b and the device array portion 15a, the overetching time and the thickness of a semiconductor layer to be overetched may be determined with reference to the endpoint detection that uses monitoring light from the accessory portion 15b.

For the duration of etching of the first stacked semiconductor layer 13a for forming a lower distributed Bragg reflector, an intensity of an optical interference waveform changes with a period of, for example, about 30 seconds. Therefore, if a periodic waveform does not appear in the optical interference waveform within 30 seconds, the etching may be judged to reach a contact layer. If the etching rate is assumed to be, for example, about 300 nm/min, the thickness of the contact layer 13i may be set to be 150 nm or more. However, when a contact layer has a thickness of more than 500 nm, the lower distributed Bragg reflector (DBR) having the contact layer has poor reflection characteristics because of light absorption in the contact layer. To achieve high reflectivity (e.g., reflectivity of 95% or more) for the DBR, the contact layer 13i preferably has a thickness of 500 nm or less. The lower limit of the controllable thickness of the contact layer is dependent on the etching rate and the window size of fast Fourier transform computation. More specifically, the lower limit of the controllable thickness of the contact layer 13i is estimated to be 50 nm.

Figure 3A:
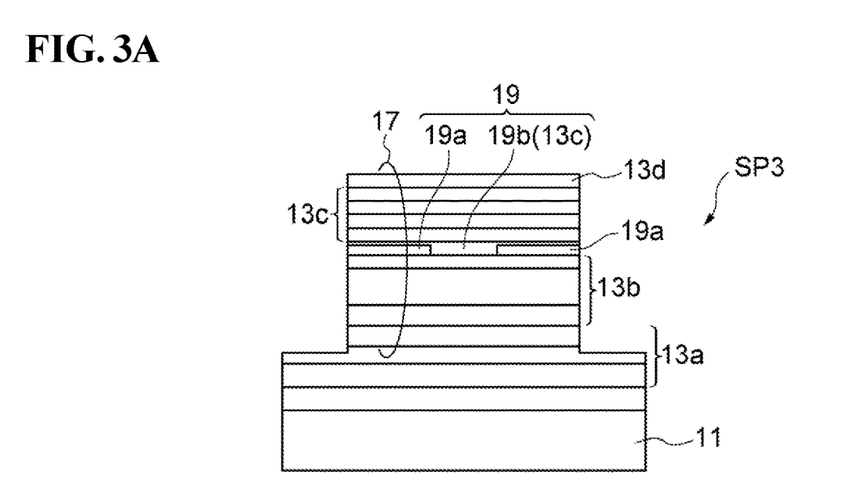
FIGS. 3A, 3B, and 3C schematically illustrate principal steps in the method for producing a semiconductor device according to this embodiment.

Next, principal steps in the method for producing a semiconductor device will be described with reference to FIGS. 3A to 3C. As illustrated in FIG. 3A, a mesa-shaped semiconductor post 17 is formed. In Step S114, a current confinement structure 19 is formed in the semiconductor post 17 in a selective oxidation process. Thus, a third substrate product SP3 is produced from the second substrate product SP2. In this embodiment, the second substrate product SP2 is inserted into an oxidation furnace to partly oxidize an Al-containing semiconductor layer 13e (e.g., AlGaAs with an Al content of 0.98 for a current confinement layer) that appears on the side surface of the semiconductor post 17. Thus, a current confinement structure 19 is formed. The peripheral portion of the AlGaAs (Al content=0.98) is oxidized into an aluminum oxide 19a. The AlGaAs remaining without being oxidized serves as a current aperture 19b.

Figure 3B:
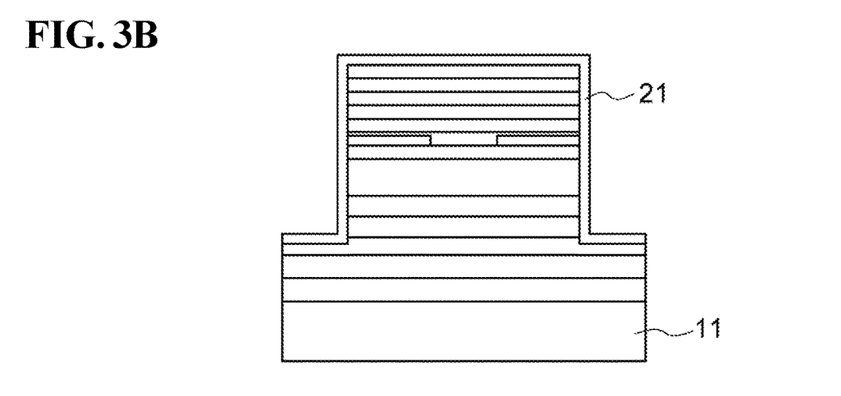

As illustrated in FIG. 3B, in Step S115, a protective film 21 is deposited on the third substrate product SP3. The protective film 21 is, for example, a silicon-based inorganic insulator. Specifically, the protective film 21 is formed of silicon dioxide, silicon nitride, or silicon oxynitride. The silicon-based inorganic insulator is formed by, for example, a chemical vapor deposition method.

Figure 3C:
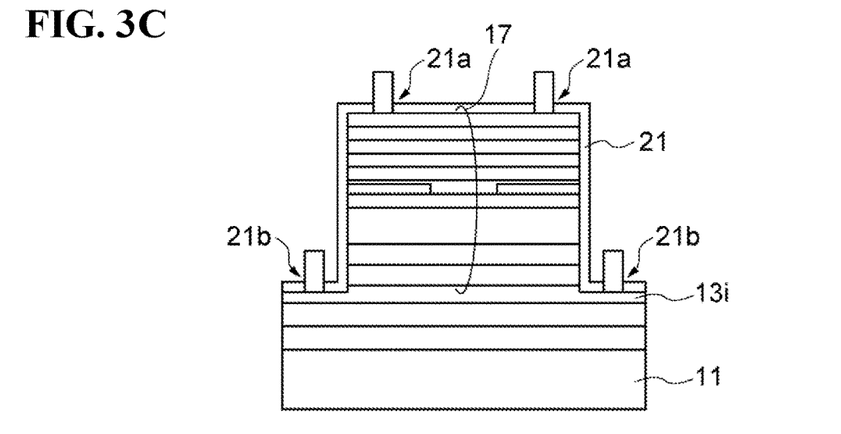

As illustrated in FIG. 3C, in Step S116, electrodes for injecting electric current into the semiconductor device are formed. Specifically, a first opening 21a and a second opening 21b are formed in the protective film 21 by performing photolithography and etching. The first opening 21a is located on an upper surface of the semiconductor post 17. The second opening 21b is located on the contact layer 13i exposed by etching. After the first opening 21a and the second opening 21b are formed, a first electrode 23a and a second electrode 23b are formed. The first electrode 23a is in contact with the upper surface of the semiconductor post 17 through the first opening 21a. The second electrode 23b is in contact with the upper surface of the contact layer 13i through the second opening 21b. The first electrode 23a has a Ti/Pt/Au stacked structure. The second electrode 23b is formed of an AuGeNi alloy. The first electrode 23a and the second electrode 23b are formed by a lift-off method.

Through these steps, a vertical cavity surface-emitting semiconductor laser is produced.

EXAMPLE

A plurality of semiconductor layers for forming a lower distributed Bragg reflector including an n-type contact layer, an active layer, an AlGaAs layer (Al content x=0.98) for current confinement, and an upper distributed Bragg reflector are grown on an insulating or n-type GaAs substrate by a metal-organic vapor phase epitaxy method. Thus, an epitaxial substrate is formed. A molecular beam epitaxial growth method may also be used for growing the semiconductor layers on the substrate. A mask for forming a semiconductor post is formed on the epitaxial substrate by photolithography. The mask is formed of a photoresist or a silicon-based inorganic insulator such as $SiO_2$ and SiN. After the mask is formed on the epitaxial substrate, the epitaxial substrate is dry-etched with an inductive coupled plasma reactive ion etching (ICP-RIE) apparatus shown in FIG. 5. The etching conditions are as follows.

Etching gas: $BCl_3$ or mixed gas of $BCl_3$ and $Cl_2$
Total flow rate of etching gas: 100 sccm (flow rate under standard conditions at 25° C.)

$BCl_3$/Ar=30 sccm/70 sccm or $BCl_3$/$Cl_2$/Ar=20/10/70 sccm

ICP power: 50 to 1000 W
BIAS power: 50 to 500 W
Substrate temperature: 25° C. or lower
Each of the lower distributed Bragg reflector and the upper distributed Bragg reflector includes an Al(x)Ga(1−x)As ($0 \leq x \leq 1$)/Al(y)Ga(1−y)As ($0 \leq x < y \leq 1$) superlattice layer. The lower distributed Bragg reflector includes a contact layer in the superlattice. The contact layer is, for example, an n-type semiconductor layer made of GaAs or Al(x)Ga(1−x)As with an Al content of $0 < x \leq 0.3$. The thickness of the contact layer is in the range of 50 nm to 500 nm. The epitaxial substrate is etched to produce a semiconductor product including a semiconductor post. Specifically, the epitaxial substrate is etched such that the etching reaches the contact layer in the lower distributed Bragg reflector. That is, the epitaxial substrate is etched until the surface of the contact layer is exposed. As a result of the endpoint detection of the etching, the thickness of the contact layer is controlled to be in the range of 40 to 490 nm.

The semiconductor product is exposed to an oxidizing atmosphere to oxidize the AlGaAs layer (Al content x=0.98). Specifically, the AlGaAs layer (Al content x=0.98) located between the active layer and the upper distributed Bragg reflector is oxidized from the side surface of the semiconductor post by supplying high-temperature water vapor into the oxidation furnace. As a result of this oxidation, an aluminum oxide layer is formed from the AlGaAs layer. The heating temperature during the oxidation is, for example, 400° C. Oxidation proceeds from the side surface of the semiconductor post toward the center of the semiconductor post, and the remaining $Al_xGa_{1-x}As$ layer (Al content x=0.98) serves as a current aperture. Through this process, a current confinement layer is formed.

After the current confinement layer is formed, a protective film is formed on an entire surface of the semiconductor product. The protective film is formed by depositing SiN, SiON, or $SiO_2$ by, for example, plasma chemical vapor deposition (CVD). The thickness of the protective film is adjusted so that the protective film serves as a passivation film and also a high reflection film for light emitted from the upper surface of the semiconductor post.

A plurality of openings are formed in the protective film by performing photolithography and etching. One of the openings is located on the upper surface of the semiconductor post. An upper electrode is formed in the opening so as to be in contact with a top layer of the semiconductor post that is, for example, a p-type semiconductor layer. The upper electrode has a Ti/Pt/Au stacked structure. The other of the openings is located on the lower contact layer exposed by the etching. A lower electrode is formed in the opening located on the lower contact layer so as to be in contact with the lower contact layer that is made of, for example, an n-type semiconductor. The lower electrode has an AuGeNi/Au stacked structure. After these electrodes are formed, the back surface of the substrate is polished to produce a product having a thickness of 100 to 200 μm. The polished product is separated into a plurality of semiconductor devices, which are vertical cavity surface-emitting semiconductor laser chips. Through these processes, a semiconductor device according to this Example is produced.

In the production of vertical cavity surface-emitting semiconductor lasers, the accuracy of the endpoint detection in the step of etching a plurality of semiconductor layers for forming the semiconductor post relates to the yield of vertical cavity surface-emitting semiconductor lasers. In the step of forming the semiconductor post, etching is stopped when the n-type lower contact layer included in the lower distributed Bragg reflector is being etched. If the n-type lower contact layer is too overetched so that etching reaches a layer below the contact layer, a desired electric contact having a low contact resistance may not be achieved. A low contact resistance between the n-type contact layer and the lower electrode contributes to an improvement in the characteristics of vertical cavity surface-emitting semiconductor lasers. A thick contact layer exhibits good contact characteristics. However, such a thick contact layer increases the light absorption in the lower distributed Bragg reflector. As a result, degradation of the optical characteristics of vertical cavity surface-emitting semiconductor lasers occurs. In order to obtain a low contact resistance and a low light absorption, it is important to control the thickness of the n-type lower contact layer. Therefore, a part of the lower contact layer having a desired thickness is left in the lower distributed Bragg reflector without being etched. A low light absorption may be achieved by controlling a thickness of the lower contact layer so as to be a thickness of 500 nm or less. When the lower contact layer in the lower distributed Bragg reflector has such a thickness, the lower distributed Bragg reflector may have a high reflectivity of 95%. The endpoint detection in the embodiment may control the thickness of the lower contact layer with high accuracy so as to have a thickness of 500 nm or less. In addition, a low contact resistance may also be achieved for the lower contact layer having such a thickness of 500 nm or less.

In the step of etching the stacked semiconductor layer including an upper distributed Bragg reflector, an active layer, and a lower distributed Bragg reflector, the Fourier transform spectrum is used during the etching. The Fourier transform spectrum is derived from an optical interference waveform by using the fast Fourier transform unit (FFT unit) 10$i$ illustrated in FIG. 5. Optical interference signals are obtained through interference between a light component reflected from an etched surface and a light component reflected from a surface of the GaAs substrate. When a stacked semiconductor layer including a superlattice for forming, for example, a distributed Bragg reflector is etched, the light intensity in an optical interference waveform periodically changes with lapse of etching time so as to draw a sine wave as a function of the etching time. The superlattice includes a plurality of semiconductor layers that are periodically stacked with a predetermined period of thickness. In the embodiment, the superlattice includes an AlGaAs/GaAs superlattice or an AlGaAs/AlGaAs superlattice, for example. The period of time in the sine wave of the optical interference waveform relates to the period of the thickness of the superlattice. In the embodiment, the superlattice for forming the lower distributed Bragg reflector includes a single semiconductor layer (lower contact layer) having a thickness of 5 to 100 nm therein. When etching of a superlattice disposed on the lower contact layer in the lower distributed Bragg reflector shifts to etching of the lower contact layer, the light intensity of an interference waveform changes so as to change the Fourier transform spectrum. Specifically, the intensity of a periodic component in the optical interference light decreases. Therefore, in the Fourier transform spectrum, the intensity of the low frequency component increases as compared with the intensity of the high frequency component corresponding to the periodic component in the optical interference light. This change in the Fourier transform spectrum notifies the end of etching of the superlattice disposed on the lower contact layer in the lower distributed Bragg reflector, and the start of etching of the lower contact layer. This change is obtained by converting the digital signals derived from an optical interference waveform into the fast Fourier transform spectrum in real time and analyzing the change in the intensity between a direct-current component and a frequency component in the fast Fourier transform spectrum.

An optical monitoring apparatus receives an interference light through a view port disposed near the ceiling of a dielectric dome of an etching apparatus (e.g., an ICP-RIE apparatus). The optical monitoring apparatus includes a light source (e.g., a halogen lamp (white light source)), a spectroscope for obtaining an optical interference waveform, a light-receiving device (photodiode (PD)) or an image pick-up device (e.g., charge-coupled device (CCD) camera), and an arithmetic unit that converts electric signals corresponding to the optical interference waveform into the fast Fourier transform spectrum. The arithmetic unit is connected to a radio frequency (RF) power supply of the ICP-RIE apparatus, and ON/OFF of the RF power supply may be controlled in response to the computational results of the arithmetic unit.

In this endpoint detection method, after the etching of a stacked semiconductor layer starts in the etching apparatus, the optical monitoring apparatus acquires an optical interference waveform. The spectroscope of the optical monitoring apparatus receives the optical interference waveform, and separates the optical interference waveform into monochromatic reflected light components. A photodiode receives one of the monochromatic reflected light components through the spectroscope, and generates electric signals. The arithmetic unit converts the electric signals into the fast Fourier transform spectrum. In the fast Fourier transform spectrum, the intensity of a periodic component at a high frequency corresponding to periodic signals in the optical interference waveform and the intensity of an aperiodic component at a low frequency (e.g. direct-current component) are monitored. The intensities of these components may have a predetermined threshold to decide the endpoint of etching. The threshold is set to, for example, a half of the intensity of the periodic component. When the intensity of the periodic component is lower than the threshold or when the intensity of the aperiodic component is higher than the threshold, the endpoint detection is determined.

By using Fourier transform method for endpoint detection in the dry etching process, a contact layer (remaining film) having a thin thickness of 150 nm or less is accurately formed in the lower distributed Bragg reflector with good reproducibility. The detection accuracy is 10 nm in terms of thickness. The electrical connection in the lower distributed Bragg reflector relates to a thickness of a contact layer left through etching for forming a semiconductor post. Thus, endpoint detection during etching is important.

Figure 8:
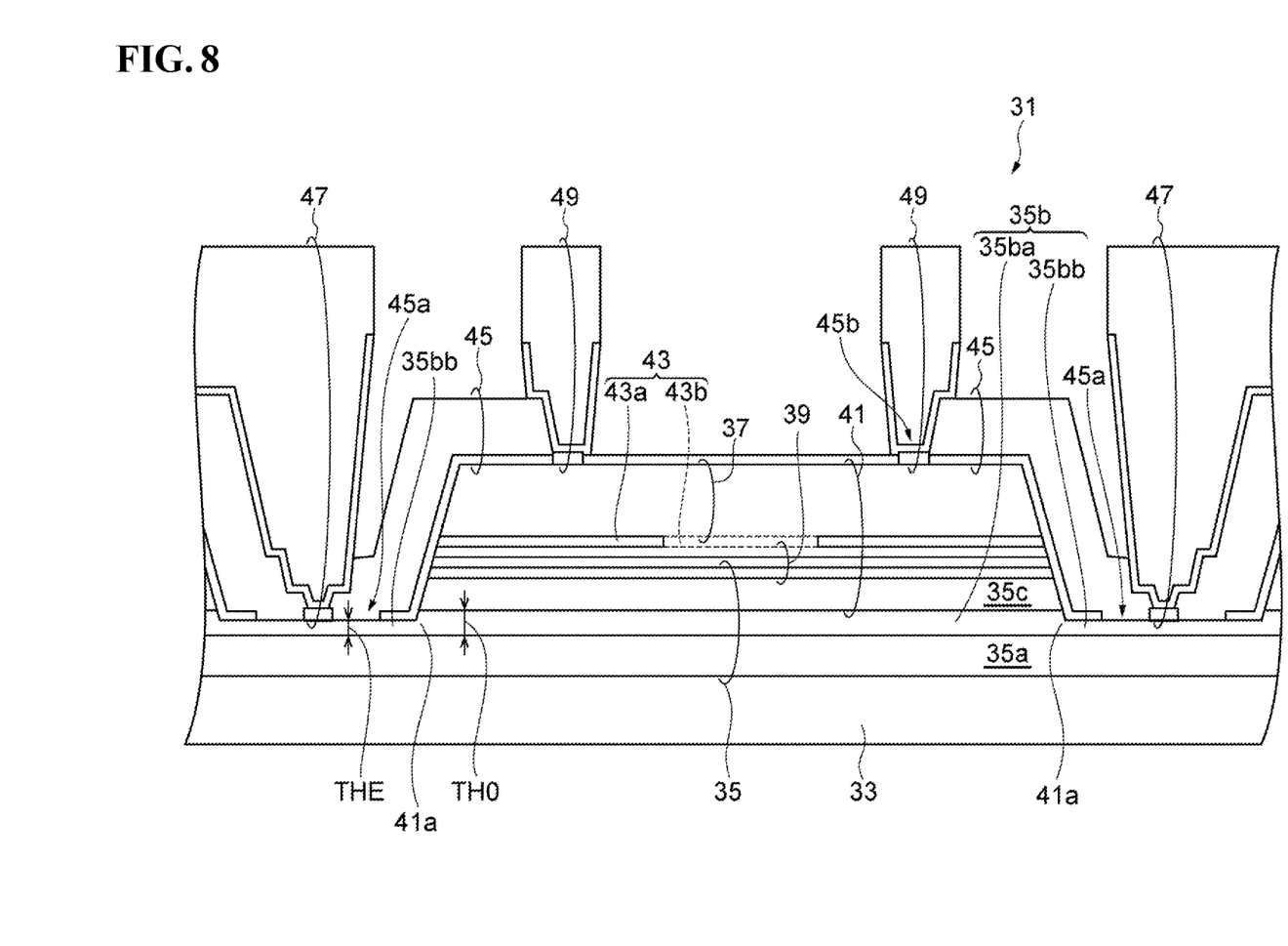
FIG. 8 schematically illustrates a vertical cavity surface-emitting laser according to this embodiment.

FIG. 8 schematically illustrates a vertical cavity surface-emitting laser (VCSEL) according to this embodiment. A vertical cavity surface-emitting semiconductor laser (VCSEL) 31 includes a substrate 33, a lower distributed Bragg reflector 35 disposed on the substrate 33, an upper distributed Bragg reflector 37 disposed above the substrate 33, and an active layer 39 disposed between the lower distributed Bragg reflector 35 and the upper distributed Bragg reflector 37. The lower distributed Bragg reflector 35 includes a first portion 35$a$, a contact layer 35$b$, and a second portion 35$c$. The first portion 35$a$ is disposed between the contact layer 35$b$ and the substrate 33. The contact layer 35$b$ is disposed between the first portion 35$a$ and the second portion 35$c$. The upper distributed Bragg reflector 37, the active layer 39, and the second portion 35$c$ of the lower distributed Bragg reflector 35 are disposed inside the semiconductor mesa 41 of the vertical cavity surface-emitting semiconductor laser 31. The semiconductor mesa 41 corresponds to the semiconductor post of the vertical cavity surface-emitting semiconductor laser 31. A bottom 41$a$ of the semiconductor mesa 41 is located in the contact layer 35$b$ of the lower distributed Bragg reflector 35. The contact layer 35$b$ includes a first region 35$ba$ disposed inside the semiconductor mesa 41 and a second region 35$bb$ disposed outside the semiconductor mesa 41. The first region 35$ba$ of the contact layer 35$b$ has a thickness TH0 of 50 nm to 500 nm. The difference between the thickness TH0 of the first region 35ba and the thickness THE of the second region 35bb of the contact layer 35b is 40 nm or less so as to provide a relatively thick second region 35bb. This difference between the thickness TH0 and the thickness THE shows the upper limit of the amount of etching.

According to this vertical cavity surface-emitting semiconductor laser 31, the upper distributed Bragg reflector 37 and the active layer 39 are disposed inside the semiconductor mesa 41. The bottom 41a of the semiconductor mesa 41 is located in the contact layer 35b of the lower distributed Bragg reflector 35. The thickness of the second region 35bb is thick enough to achieve a low contact resistance when an electrode is formed on the second region 35bb. As a result, an electrode 47 formed on the second region 35bb of the contact layer 35b has a low contact resistance. On the other hand, the first region 35ba in the semiconductor mesa 41 has a desired thickness without etching so that the lower distributed Bragg reflector has high reflectivity.

The vertical cavity surface-emitting semiconductor laser 31 includes a current confinement layer 43 disposed in the semiconductor mesa 41. The current confinement layer 43 includes an oxide layer 43a and a semiconductor layer 43b surrounded by the oxide layer 43a. An electric current injected into the vertical cavity surface-emitting semiconductor laser 31 is provided to the active layer 39 through the semiconductor layer 43b. A passivation film 45 covers a surface of a semiconductor region including the semiconductor mesa 41. The passivation film 45 includes a first opening 45a at the bottom of a groove that defines the semiconductor mesa 41. The lower electrode 47 is in contact with the second region 35bb (the contact layer 35b outside the semiconductor mesa 41) through the first opening 45a. The passivation film 45 has a second opening 45b on an upper surface 41b of the semiconductor mesa 41. An upper electrode 49 is in contact with the upper surface 41b of the semiconductor mesa 41 through the second opening 45b.

The contact layer in the lower distributed Bragg reflector is formed of GaAs or Al(x)Ga(1−x)As with an Al content of $0 < x \leq 0.3$. In the embodiment, the contact layer is made of Al(x)Ga(1−x)As (x=0.10). The lower distributed Bragg reflector includes an AlGaAs/GaAs superlattice or an AlGaAs/AlGaAs superlattice.

Specifically, the lower distributed Bragg reflector includes the following.
Basic structure (for a single period) in the periodic structure on the active layer side (e.g. second portion 35c):
   Al(x)Ga(1−x)As, thickness 38.0 nm, x=0.15
   Al(x)Ga(1−x)As, thickness 25.0 nm, x=0.50
   Al(x)Ga(1−x)As, thickness 45.0 nm, x=0.90
   Al(x)Ga(1−x)As, thickness 25.0 nm, x=0.50
Contact layer (e.g. contact layer 35b):
   Al(x)Ga(1−x)As, thickness 500.0 nm, x=0.10
Basic structure (for a single period) in the periodic structure on the substrate side (e.g. first portion 35a):
   Al(x)Ga(1−x)As, thickness 38.0 nm, x=0.15
   Al(x)Ga(1−x)As, thickness 25.0 nm, x=0.50
   Al(x)Ga(1−x)As, thickness 5.0 nm, x=0.90
   Al(x)Ga(1−x)As, thickness 35.0 nm, x=0.90
   Al(x)Ga(1−x)As, thickness 5.0 nm, x=0.90
   Al(x)Ga(1−x)As, thickness 25.0 nm, x=0.50

Figure 9:
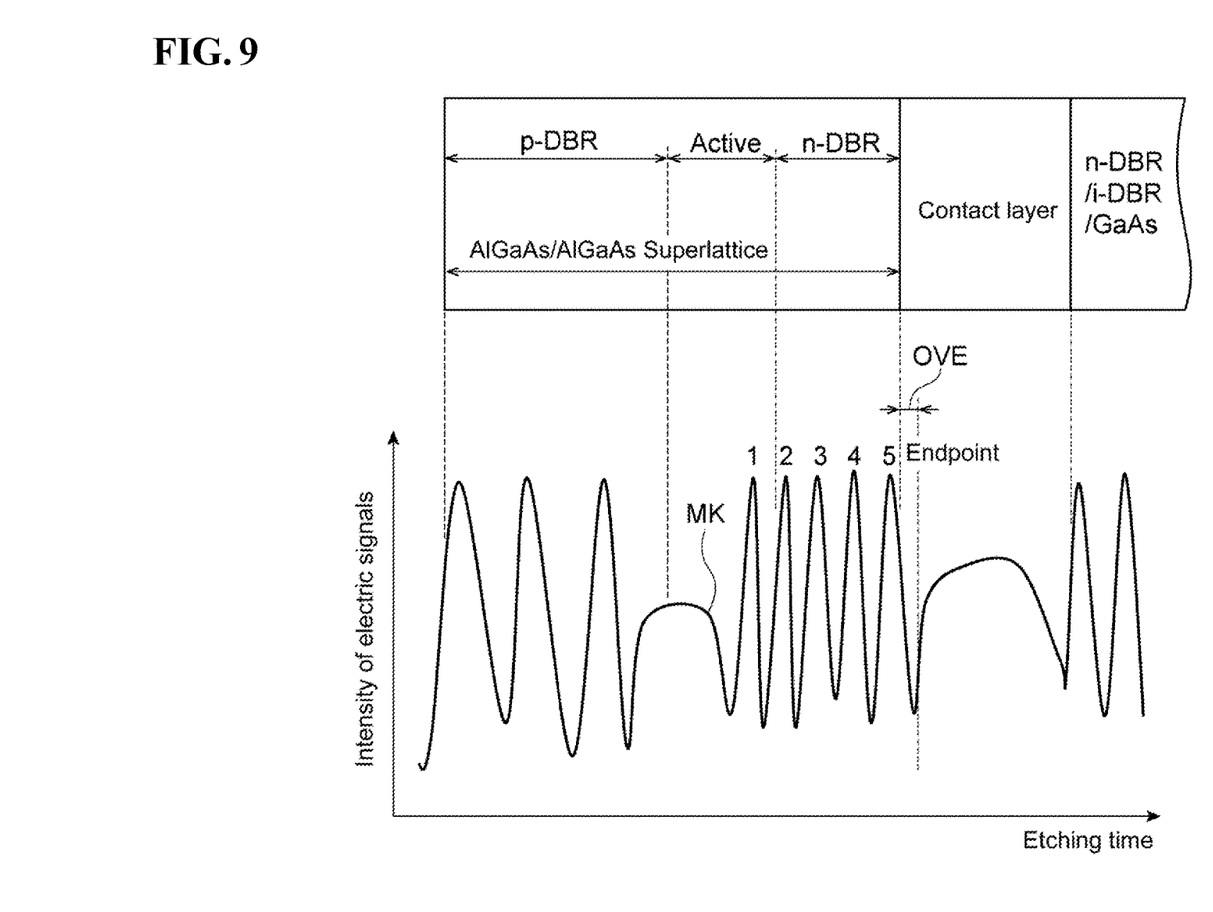
FIG. 9 illustrates a signal waveform in a production method in which the endpoint is determined by counting the number of peaks that appear in an interference light waveform.

FIG. 9 illustrates a signal waveform in a production method in which the endpoint is determined by counting the number of peaks that appear in an interference light waveform. In this method, when the surface of a substrate product is etched, an error occurs in counting the number of peaks when the optical interference waveform changes due to a film made of dirt or the like formed on the surface. Furthermore, a dedicated semiconductor layer (MK) from which the number of peaks is counted needs to be disposed in a multilayer epitaxial region. The count of the number of peaks starts at the time when the dedicated semiconductor layer (MK) is etched.

In preferred embodiments, principles of the present invention have been described with reference to the drawings. However, those skilled in the art understand that the present invention can be changed in arrangement and details without departing from the principles. The present invention is not limited to the specific configurations disclosed in the embodiments. Therefore, the Claims and all the modifications and changes within the spirit of the Claims are claimed as the invention.

What is claimed is:

1. A method for producing a semiconductor device, the method comprising the steps of:
   providing a substrate product including a substrate and a first stacked semiconductor layer disposed on the substrate, the first stacked semiconductor layer including a first portion, a contact layer, and a second portion with the contact layer being disposed between the first portion and the second portion, and with the second portion being disposed between the contact layer and the substrate, each of the first portion and the second portion having a plurality of semiconductor layers of different compositions that are alternately and periodically stacked with a predetermined period;
   forming a mask on the substrate product; and
   etching the first stacked semiconductor layer using the mask,
   wherein the step of etching the first stacked semiconductor layer includes the steps of:
   optically monitoring an optical signal including an interference component that is obtained through interference between a light component reflected from an etched surface of the substrate product and a light component reflected from a boundary within the substrate product for detecting an endpoint of etching;
   converting the optical signal to an electric signal to generate a monitoring signal;
   performing Fourier transform on the monitoring signal to generate a spectrum signal, the spectrum signal including a frequency component corresponding to the period of the semiconductor layers in the first portion of the first stacked semiconductor layer;
   determining the endpoint of etching by using the spectrum signal provided by the Fourier transform; and
   stopping etching within the contact layer by detecting a change in the spectrum signal.

2. The method for producing a semiconductor device according to claim 1,
   wherein the interference component is obtained through interference between the light component reflected from the etched surface and a light component reflected from a surface of the substrate as the light component reflected from the boundary.

3. The method for producing a semiconductor device according to claim 1, wherein
   the substrate product includes a device area and an accessory area,
   the mask has a plurality of patterns including openings, one of the patterns being on the device area and one of the patterns being on the accessory area, the pattern on the accessory area has a larger opening than that of the pattern on the device area so that the accessory area is etched at a larger etching rate than that of the device area, and the light component reflected from the etched surface is reflected from the accessory area.

4. The method for producing a semiconductor device according to claim 1, wherein the substrate product includes an active layer that generates light, and the first stacked semiconductor layer is disposed between the substrate and the active layer.

5. The method for producing a semiconductor device according to claim 4, wherein the substrate product includes a second stacked semiconductor layer disposed on the substrate, the second stacked semiconductor layer including a plurality of semiconductor layers having different compositions that are alternately and periodically stacked, the active layer is disposed between the first stacked semiconductor layer and the second stacked semiconductor layer, and each of the first stacked semiconductor layer and the second stacked semiconductor layer has a periodic structure that constitutes a distributed Bragg reflector.

6. The method for producing a semiconductor device according to claim 1, wherein the contact layer has a thickness larger than a thickness of any of the semiconductor layers that are alternatively and periodically stacked.

* * * * *